United States Patent [19]

Mikhail

[11] Patent Number: 5,383,937
[45] Date of Patent: Jan. 24, 1995

[54] RECESSED PATELLAR PROSTHESIS

[76] Inventor: W. E. Michael Mikhail, 4203 Shamley Green, Toledo, Ohio 43623

[21] Appl. No.: 22,997

[22] Filed: Feb. 26, 1993

Related U.S. Application Data

[63] Continuation-in-part of Ser. No. 599,432, Oct. 18, 1990, Pat. No. 5,197,986, which is a continuation-in-part of Ser. No. 508,088, Apr. 11, 1990, abandoned.

[51] Int. Cl.$^6$ .............................................. A61F 2/38
[52] U.S. Cl. .................................................. 623/20
[58] Field of Search .................... 623/16, 18, 19, 20, 623/22, 23

[56] References Cited

U.S. PATENT DOCUMENTS

| | | | |
|---|---|---|---|
| 3,765,033 | 10/1973 | Goldberg et al. | 623/20 |
| 3,878,566 | 4/1975 | Bechtol | 623/20 |
| 4,081,866 | 4/1978 | Upshaw et al. | 623/20 |
| 4,158,894 | 6/1979 | Worrell | 623/20 |
| 4,276,660 | 7/1981 | Laure | 623/20 |
| 4,462,120 | 7/1984 | Rambert et al. | 623/20 |
| 4,769,039 | 9/1988 | Horber | 623/20 |
| 4,822,366 | 4/1989 | Bolesky | 623/20 |
| 4,964,867 | 10/1990 | Boger | 623/20 |
| 4,979,957 | 12/1990 | Hodorek | 623/20 |
| 5,019,104 | 5/1991 | Whiteside et al. | 623/20 |
| 5,032,132 | 7/1991 | Matsgu, III et al. | 623/20 |
| 5,197,986 | 3/1993 | Mikhail | 623/20 |

FOREIGN PATENT DOCUMENTS

| | | |
|---|---|---|
| 0307654 | 3/1989 | European Pat. Off. |
| 2625096 | 11/1988 | France . |
| 2615096 | 4/1989 | France . |
| 1522497 | 8/1978 | United Kingdom . |

OTHER PUBLICATIONS

Supplementary Partial European Search Report EP 91 90 5698.
Catalog of Biomet, Inc., Warsaw, Ind., entitled "AGC Total Knee System–Patellar Femoral Systems".
"Patellar Prosthesis Positioning in Total Knee Arthroplasty" by Luis Gomes et al., *Clinical Orthopaedics and Related Research*, Nov. 1988, pp. 72–81.
Smith + Nephew Richards publication entitled "Genesis ™ Total Knee System—Cruciate-Retaining Primary Technique–Surgical Technique".
Catalog of Dow Corning Wright, Arlington, Tenn., copyright 1989 entitled, "Whiteside Ortholoc ® Modular Knee System".
Catalog of Intermedics Orthopedics, Inc. Austin, Tex., copyright 1987 entitled "The Intermedics Natural-Knee ® System with Cancellous-Structured Titanium ™ ".
Catalog of DePuy, Warsaw, Ind., division of Boehringer Mannheim Corporation, copyright 1988, entitled "The AMK ™ Total Knee System–Design Rationale and Surgical Procedure", pp. 13 and 47.

*Primary Examiner*—David Isabella
*Attorney, Agent, or Firm*—Emch, Schaffer, Schaub & Porcello

[57] ABSTRACT

A patellar prosthesis has a dome and a body having a central post and an outwardly facing surface tapering toward said dome in a direction extending away from said central post. A plurality of cavities are formed in said body outwardly facing surface. The cavities include an undercut wall for retention of bone cement upon implantation in a prepared patella.

20 Claims, 5 Drawing Sheets

RECESSED PATELLAR PROSTHESIS

This is a continuation-in-part of application Ser. No. 07/599,432, filed Oct. 18, 1990 now U.S. Pat. No. 5,197,986, which is a continuation-in-part of application Ser. No. 07/508,088, filed Apr. 11, 1990, now abandoned.

BACKGROUND ART

In total knee arthroplasty it is customary to resurface the articulating ends of the femur and the tibia with prostheses which are fastened to the cut and prepared ends of the femur and tibia. One such prosthesis is that described in a catalog published by Johnson & Johnson Orthopaedics Inc. entitled "P.F.C. Total Knee System" (P.F.C. is a registered trademark of Johnson & Johnson Orthopaedics Inc.) using a surgical technique described in a booklet published by Johnson & Johnson Products entitled "Surgical Technique—The Press Fit Condylar Total Knee System with Specialist Instruments." Another such prosthesis is described in U.S. Pat. No. 4,822,366.

One component of the P.F.C. Total Knee System and virtually every other total knee replacement system utilized is a patellar component.

Heretofore great difficulty has been encountered in providing a patellar component which will endure, for extended periods of time, the rigors to which such components are placed. Thus, a patellar component is subjected to continual rubbing against the femoral component of the prosthesis with each flexing movement of the leg. As a result, the patellar component may wear to an extent as to impede function of the knee even though the other components may not be worn out. In addition, it may also cause undue wear on the other components of a total knee system.

In a total knee system, the patellar component is typically a dome-shaped member which is implanted on a flat surface or a recess cut into the patient's patella. The patellar implant may either be all plastic, typically high molecular weight polyethylene (HMWPE) or plastic with a metal backing formed of titanium, chrome-cobalt alloy, stainless steel or the like.

In addition to the patellar implant shown in the Johnson & Johnson Orthopaedics brochure entitled "P.F.C. Total Knee System", other types of patellar implants are disclosed in catalogs published by Dow Corning Wright entitled "Whiteside Ortholoc Modular Knee System" and published by DePuy, Warsaw, Ind., a Division of Boehringer Mannheim Corporation, entitled "The AMK Total Knee System".

As will be appreciated, it is desirable to utilize a patellar implant which combines the advantages of requiring a minimal amount of cutting of the patella, secure placement of the patellar implant and the ability to easily remove such implant in the event revision is required.

Accordingly, it is an object of the present invention to provide a patellar prosthesis for use in combination with the prepared patella bed in which minimal amount of the patient's natural patella is required to be removed.

It is a further object of the present invention to provide a patellar prosthesis designed for implantation in a patella which can be replaced with minimal damage to the patella in the event revision is required.

DISCLOSURE OF INVENTION

The present invention relates to a new and improved patellar implant formed completely from plastic having a domed portion intended to face outwardly from the patella for engagement with the condylar or trochlear groove of a femoral prosthesis component, a body portion and a central post extending from said body portion away from the domed portion and intended to be fixedly secured within a recess cut into the patella. A plurality of retention cavities having an undercut wall are provided to ensure proper fixation.

BEST MODE FOR CARRYING OUT INVENTION

Figure 1:
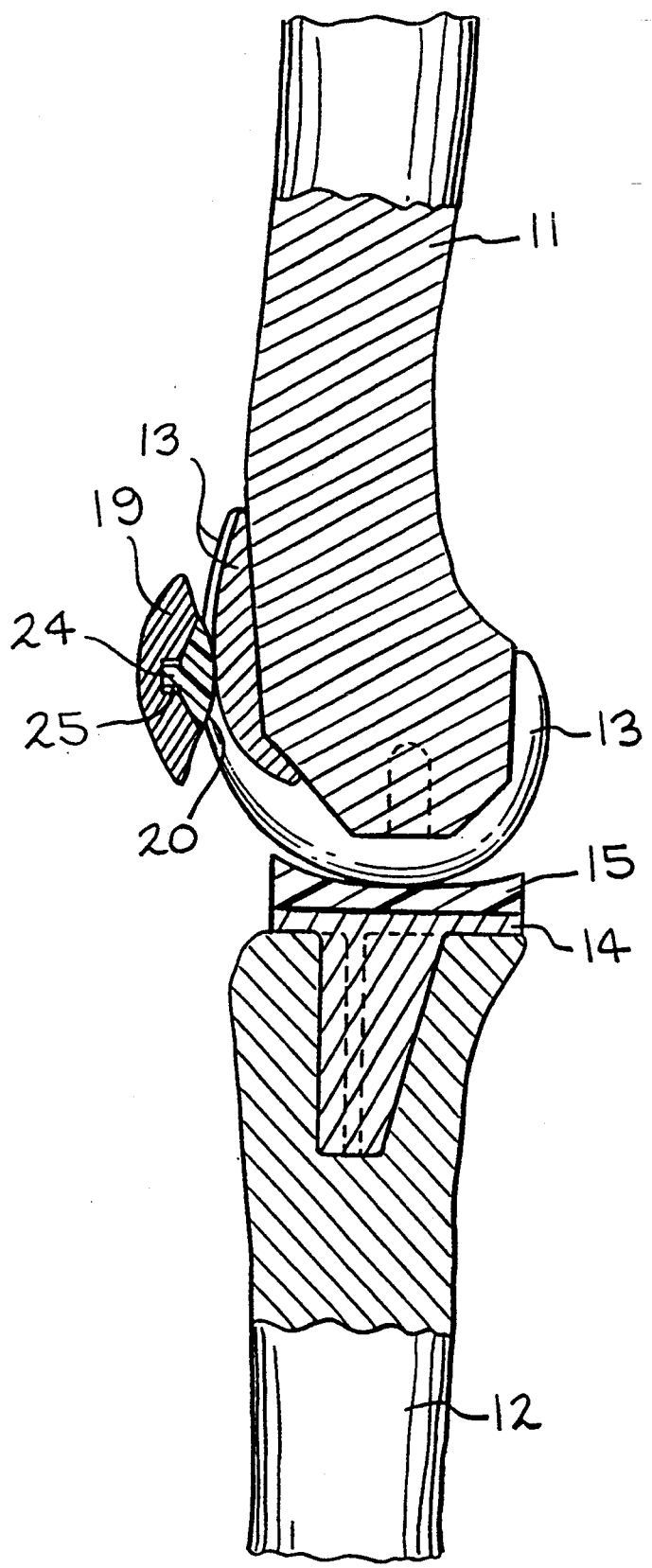
FIGS. 1 is a schematic view partly in section of a total knee system implanted in the leg of a patient and showing specifically the position of the patella with the patellar implant of the present invention articulating with the femoral component of the implant.

Referring now to the drawings, there is shown in FIG. 1, a leg including the femur 11 and tibia 12 to which a total knee prosthesis has been implanted including a femoral implant 13, a tibial base implant 14 and a tibial insert 15. Typically, the femoral implant 13 and tibial base implant 14 are formed of metal such as titanium alloy or chrome-cobalt while the tibial insert 15 is formed of plastic such as high molecular weight polyethylene (HMWPE).

There is also shown a patella 19 having implanted therein a patellar implant generally designated by the number 20 of the present invention.

In the embodiment disclosed in FIGS. 1, 2, 3 and 5-7, the patellar implant 20 is formed as a unitary body and includes a dome-shaped portion 21, facing outwardly for engagement with the femoral implant 13.

Figure 5:
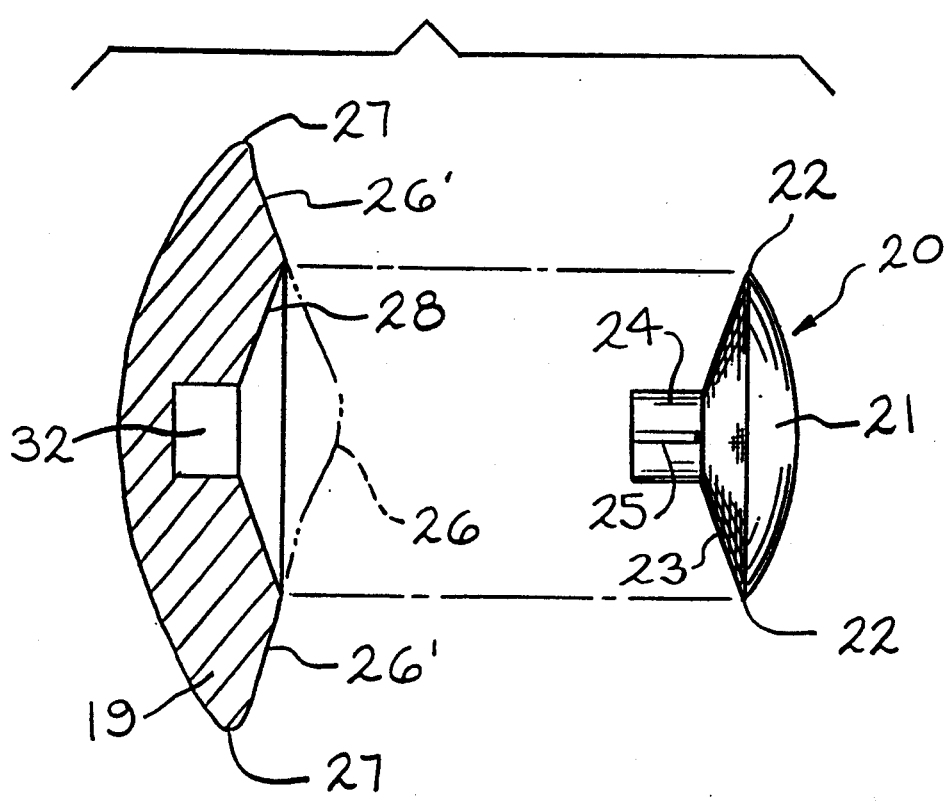
FIG. 5 is a view showing schematically a patella in section following osteotomy to prepare it for receiving the implant of the present invention and showing, removed therefrom, the patellar implant of the present invention.
Figure 6:
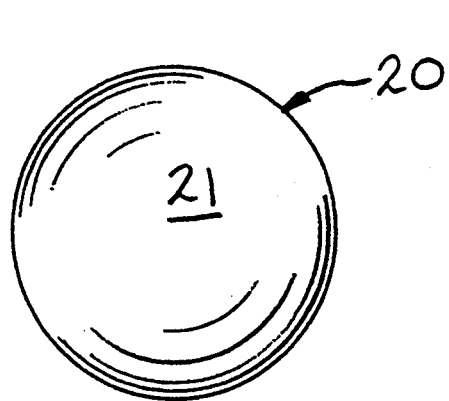
FIG. 6 is a top plan view of the patellar implant of the present invention.
Figure 7:
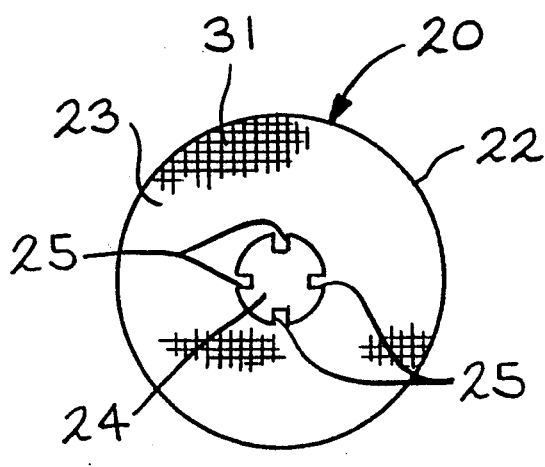
FIG. 7 is a bottom view of the patellar implant of the present invention showing the post including the longitudinal grooves.

As can be seen in FIG. 5, the patella 19, prior to osteotomy to prepare it to receive the patellar implant 20, included a natural dome 26 which must be removed. Some resection procedures require that the entire dome 26 be removed completely to the peripheral edge 27. Others require that only the central portion of the dome 26 be removed. A major advantage of the patellar implant 20 of the present invention is that it may be implanted with a minimal amount of bone removed from the patella 19. Thus, the patella 19 is prepared to receive the patellar implant 20 so as to leave intact the outer portions 26' of the dome 26 of the patella 19.

Figure 3:
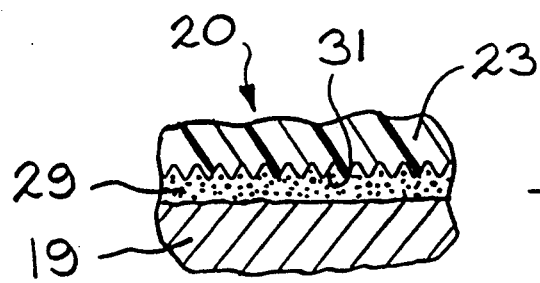
FIG. 3 is a sectional view taken through line 3—3 of FIG. 2.

The dome 21 of the patellar implant 20 has a peripheral edge 22 which, upon implantation is to meet smoothly with the outer portion 26' of the patella 19. Tapering inwardly from the peripheral edge 22 in a direction away from the dome 21 is a conical-shaped body portion 23 from which a central post 24 extends. The post 24 has a plurality of longitudinal grooves 25. As can be seen in FIG. 3, the patellar implant 20 is retained in the prepared patella 19 by polymethylmethacrylate (PMMA) cement 29 or other suitable bone cement. Preferably, the surface of the conical tapered body portion 23 is formed with a roughened, grooved or waffle type surface 31 to enhance retention with the PMMA cement 29.

In the osteotomy to prepare it, the patella 20 has cut therein a cavity including a first conical-shaped section 28 slightly sized and shaped to receive the conical-shaped body portion 23 of the patellar implant 20 so that the peripheral edge 22 of the dome 21 will meet smoothly with the remaining upper surface of the outer portion 26' of the patella dome.

The cavity also includes a lower cylindrical section 32 having a diameter slightly larger than the diameter of the post 24 and a depth slightly greater than the length of the post 24.

Immediately prior to implantation of the patellar implant 20, a suitable quantity of PMMA cement is placed in the cavity sections 28 and 32 and the patellar implant 20 is then forced into such cavity sections with the PMMA cement being, in effect, compression molded around the post 24, into the grooves 25 and along the face 23 of the conical body including the waffle surface 31 to firmly retain the patellar implant 20 therein. As will be appreciated, the presence of the grooves 25 in the stem 24 retained firmly by the PMMA cement serves to rotationally fix the patellar implant 20 in place.

In the event it is required to replace the patellar implant 20, it will be possible to drill a passageway into the solid post 24 in order to provide means to engage a retriever instrument to such patellar implant 20. In this way the patellar implant 20 may be removed with minimal damage to the patella 19.

As will be appreciated, the presence of the conical tapered surface on the body portion 23 will permit easier removal and yet will provide suitable retention within the conical-shaped cavity 28 to provide good fixation when combined with the fixation of the post 24 in the cylindrical section 32. As previously mentioned, significant advantage of the patellar implant 20 shown in FIG. 2 over the prior art resides in the fact that, by virtue of the tapered surface, a smaller amount of bone material is removed from the patella 19 without compromising the sound fixation of the patellar implant 20.

Figure 4:
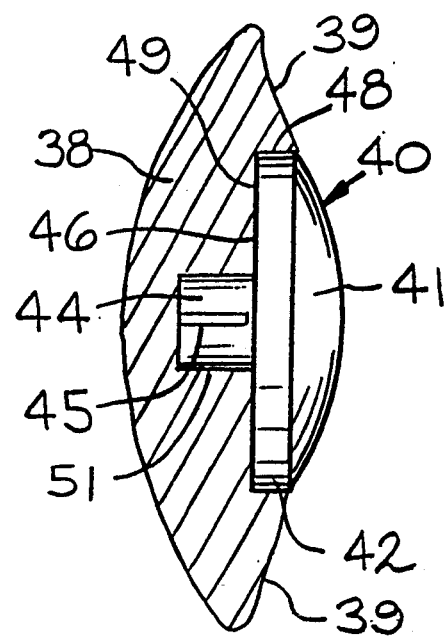
FIG. 4 is a view similar to the view of FIG. 2 showing a modified patellar implant.
Figure 2:
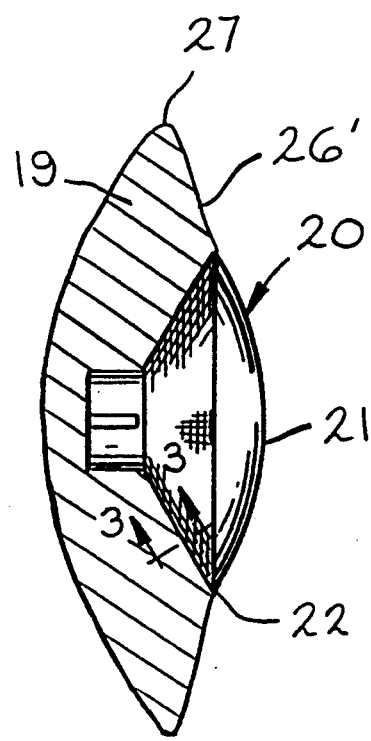
FIG. 2 is a view of one embodiment of the present invention showing the patellar implant of the present invention implanted in a patella.

Referring now to FIG. 4, there is provided a modified patellar implant 40 secured to a patella 38 which has been prepared specifically to receive it. The modified patellar implant 40 has a dome 41 facing outwardly for engagement. As in the previous embodiment, the patella 38 is prepared to receive the implant in such manner as to leave the outer portions of the dome 39 intact. The patellar implant 40 includes a short cylindrical body section 42 extending from the dome-shaped portion 41 and a central post 44 depending from the cylindrical section 42. The post 44 has a plurality of longitudinal grooves 45, preferably three or four in number. The cylindrical body section 42, opposite the dome-shaped portion 41, has a generally planar face 46 from which the post 44 extends. Preferably the planar face 46 is roughened or formed with a series of ridges or grooves in a waffle or other configuration to enhance bonding.

In the osteotomy to prepare it, the patella 39 has drilled therein a cavity including a first cylindrical-shaped section 48 slightly larger in diameter than the diameter of the cylindrical section 42 of the patellar implant 40 and having a depth substantially equal to the height of such cylindrical section 42 so that when the planar bottom face 46 of such cylindrical section 42 rests against the planar face 49 of the first cylindrical-shaped section 42, the peripheral edge of the dome 41 will meet smoothly with the remaining upper surface 39 of the patella dome. The drilled cavity also includes a lower cylindrical section 51 having a diameter slightly larger than the diameter of the post 44 and a depth slightly greater than the length of the post 44.

Immediately prior to implantation of the patellar implant 40, a suitable quantity of PMMA cement is placed in the cavity sections 48 and 51 and the patellar implant 40 is then forced into such cavities with the PMMA cement being, in effect, compression molded around the post 44 and into the grooves 45, along the planar bottom face 46 and around the edge of the cylindrical section 42 to firmly retain the patellar implant 40 therein. As will be appreciated, the presence of the grooves 45 retained by the PMMA cement assists in rotationally fixing the patellar implant 40 in place.

Figure 8:
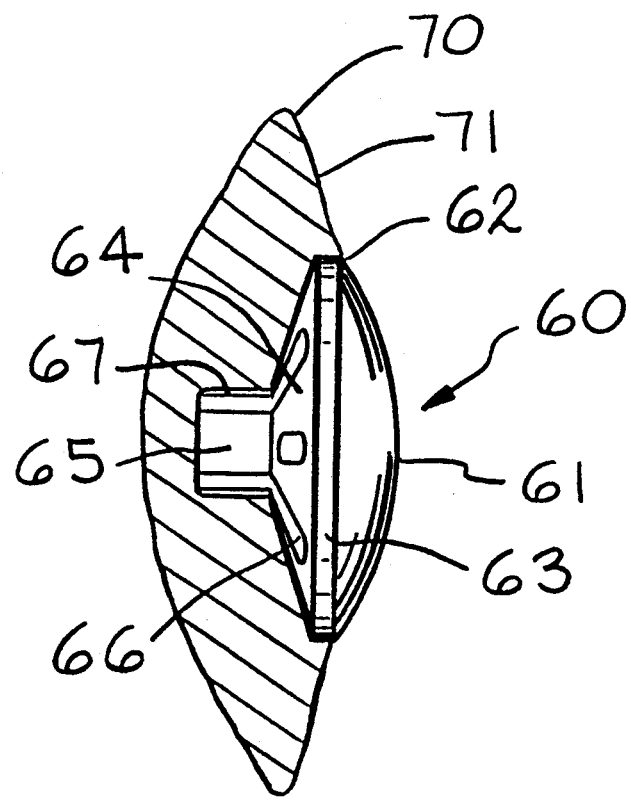
FIG. 8 is a view similar to FIG. 2 showing a further modified patellar implant.
Figure 9:
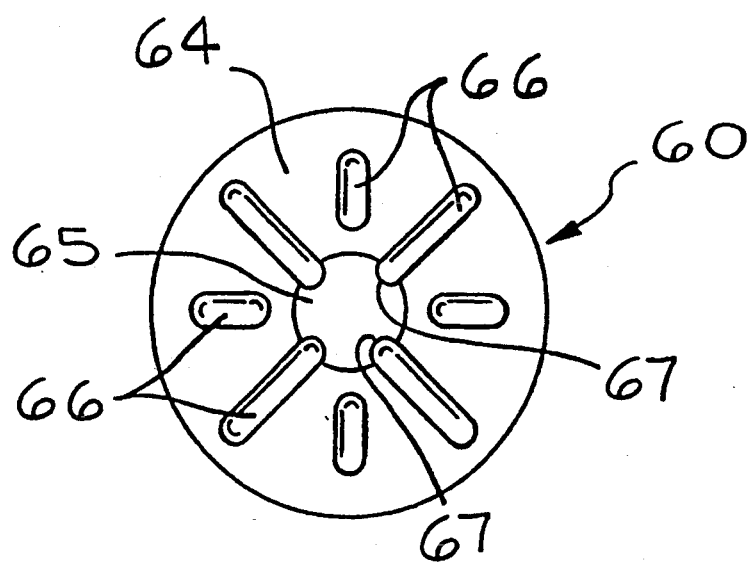
FIG. 9 is a view similar to FIG. 7 showing the further modified patellar implant of FIG. 8.
Figure 10:
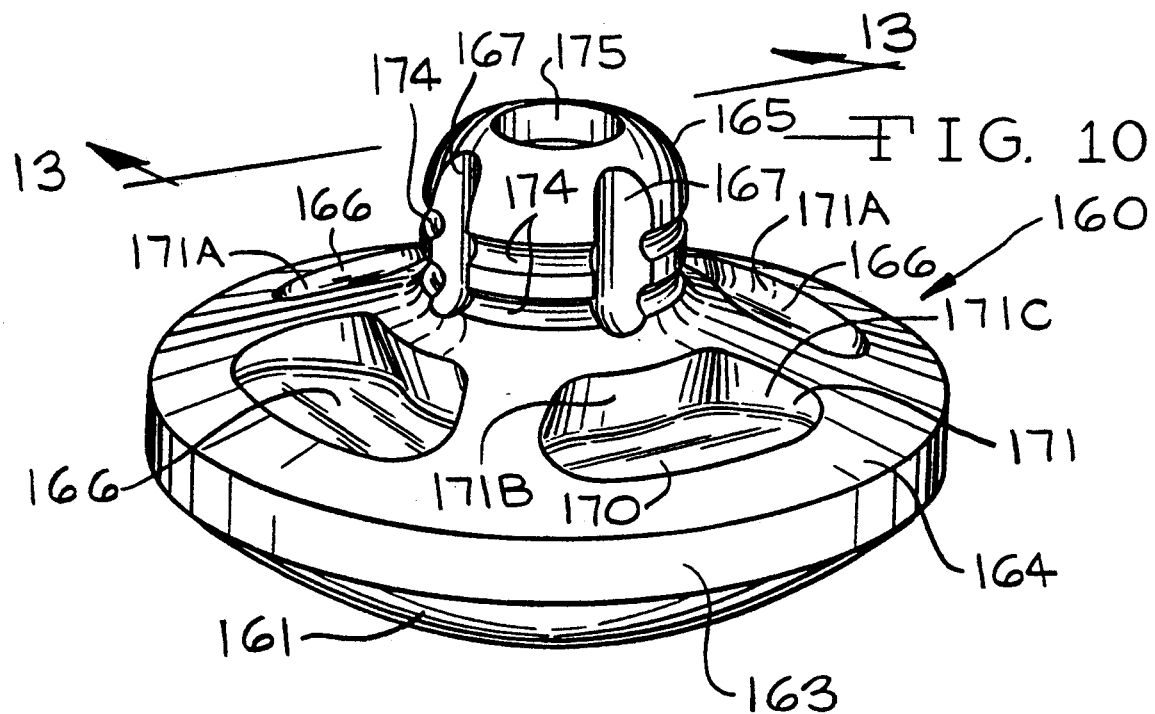
FIGS. 10-12 are perspective views of yet another embodiment of patellar implant.
Figure 11:
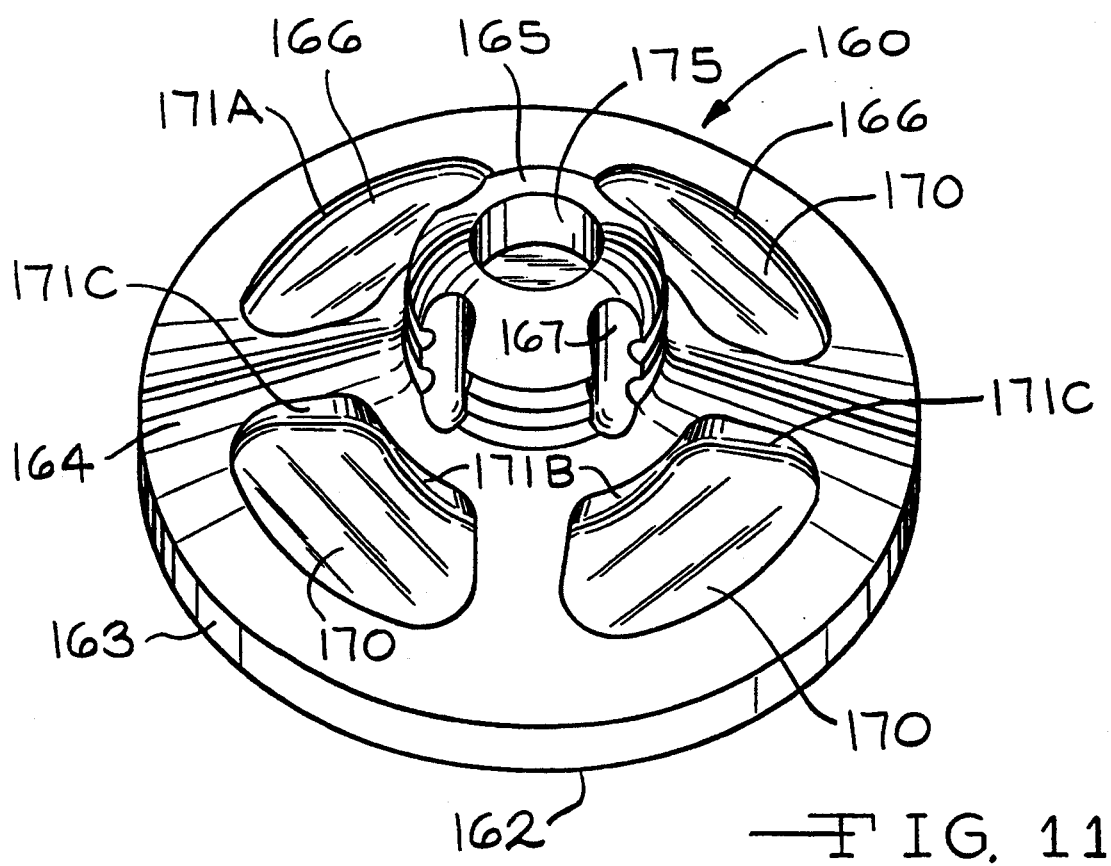
Figure 12:
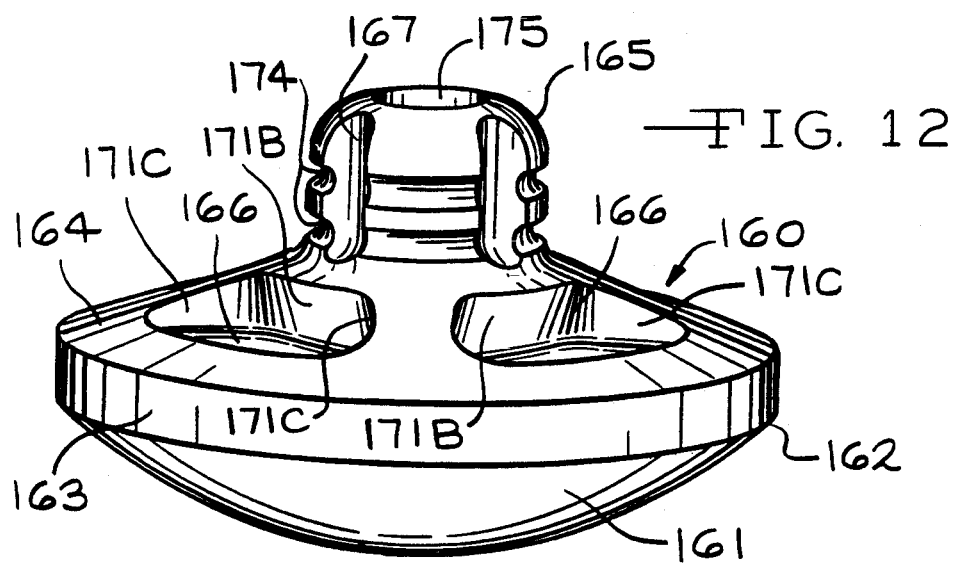
Figure 13:
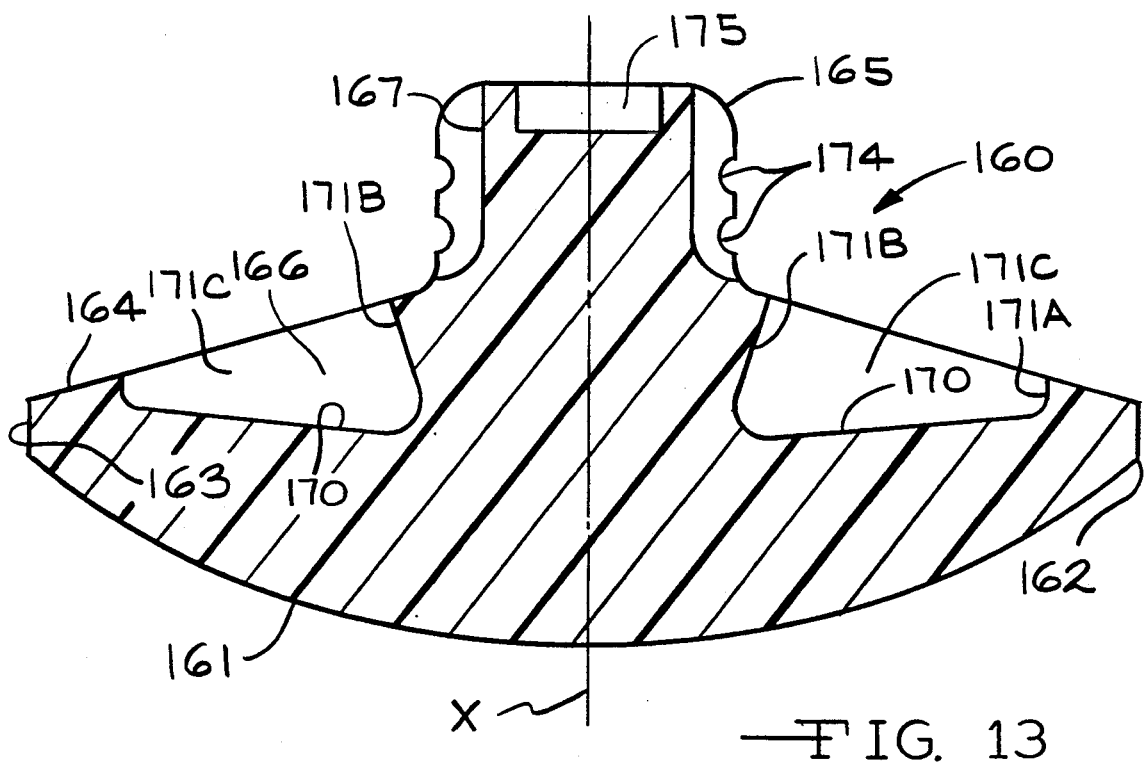
FIG. 13 is a sectional view taken through line 13—13 of FIG. 10.

Referring now to FIGS. 8 and 9, there is provided a further modified patellar implant 60 designed to be secured to a patella 70 having a dome 71 which has been specifically prepared to receive it. This embodiment of the patellar implant 60 has a dome 61 facing outwardly for engagement with the femoral implant 13 similar to the dome 21 of the embodiment shown and described in FIG. 2. The dome 61 extends radially outwardly to a peripheral edge 62 which following implantation, meets the dome 71 of the natural patella 70 in a smooth line of juncture. The patellar implant 60 includes a short cylindrical body section 63 extending from the edge 62 in a direction away from the dome 61 and a conical-shaped body portion 64 tapering away from the dome 61. A central post 65 depends from the conical tapered body portion 64.

Preferably, the surface of the conical tapered body portion 64 has formed therein a plurality of grooves 66 intended to assist in locking the patellar implant 60 firmly in place. Additionally, the post 65 may be provided with a series of longitudinal grooves 67 as in the previous embodiment.

In preparing the patella 70 to receive the patellar implant 60, initially the top of the dome 71 is cut to provide a flat surface. It is not necessary that a large portion of such dome 71 be removed but only enough to provide a flat surface to permit the drill and reamer to be accurately guided. After cutting, the patella 70 is drilled and reamed to provide a cavity shaped to receive the patellar implant 60 so that, with cement placed therein, upon implantation the patellar implant peripheral edge 62 will meet smoothly with the natural patella dome 71.

While the body portion 64 has been described as having a conical-shaped section, it should be understood that other configurations may be utilized provided the surface of such body portion tapers away from the dome 61 thereby ensuring that a minimal amount of the human patella 70 is removed in preparing the patellar implant 60 for implantation.

Referring now to FIGS. 10-13, there is provided yet another embodiment of patellar implant 160. This embodiment of the patellar implant 160 has a dome 161 facing outwardly for engagement with the femoral implant similar to the dome 21 of the embodiment shown and described in FIG. 2. The dome 161 extends radially outwardly to a peripheral edge 162. The patellar implant 160 includes a short cylindrical body section 163 extending from the edge 162 in a direction away from the dome 161 and a conical-shaped body portion 164 tapering away from the dome 161. A central post 165 depends from the conical tapered body portion 164 along an axis X.

Preferably, the surface of the conical tapered body portion 164 has formed therein a plurality of concavities 166 each of which has a reverse taper or undercut intended to assist in locking the patellar implant 160 firmly in place. Thus, each concavity 166 includes a substantially flat bottom 170 which is recessed from the tapered body portion 164 and is disposed at a small angle to or perpendicular to the axis X. The bottom 170 is joined to the tapered body portion 164 by annular wall having a front portion 1 71A generally parallel to and spaced from the edge 162, a rear portion 171B spaced further from the edge 162 than said front portion 171A and a pair of end portions 171C joining said front portion 171A with said rear portion 171B. As can be seen particularly in FIG. 13, the rear portion 171B has a reverse taper such that it is angled inwardly toward the axis X as it extends downwardly (as viewed in the Figures) from the body portion 164 to the bottom 170. As will be appreciated, when the patellar implant 160 is positioned in bone cement in the prepared cavity of the patella, the bone cement will flow into the concavity 166 and into contact with the reverse tapered rear portion 171B and thus be firmly retained in place. The bottom 170 and the front portion 171A, rear portion 171B and end portions 171C of the annular wall may be smooth or may have a granular or roughened surface to provide increased gripping by the bone cement.

As in the previous embodiment, the post 165 may be provided with a series of longitudinal grooves 167. Additionally, the post 165 has a pair of annular grooves 174 and a hollowed out central recess 175 which provide areas in which bone cement can flow for added retention upon implantation.

While the body portion 164 has been described as having a conical-shaped section, it should be understood that other configurations may be utilized provided the surface of such body portion tapers away from the dome 161 as it approaches the central post 165 thereby ensuring that a minimal amount of the human patella is removed in preparing the patellar implant 160 for implantation.

The patellar implant of the present invention is one which provides superior performance and retention upon implantation.

Many other modifications will become readily apparent to those skilled in the art. Accordingly, the scope of this invention should be limited only by the scope of the appended claims.

I claim:

1. A one-piece patellar prosthesis adapted to be implanted in a prepared patella with bone cement comprising:
   (a) a dome having an outwardly facing surface, convexly curved throughout, positioned for sliding engagement with a femoral prosthesis, said dome terminating at its radial outer extent in a circular edge defining a plane, said dome having a central axis perpendicular to said plane;
   (b) a body having a surface facing away from said outwardly facing surface, said body extending to said circular edge and said body surface having (i) a first central area in proximity to said central axis spaced from said plane by a predetermined amount, (ii) other areas extending radially outwardly from said central axis tapering without interruption toward said plane and (iii) at least one concavity positioned between said other areas, said concavity having reverse taper surfaces for engagement with said bone cement; and
   (c) post means extending from said body surface along said central axis.

2. A patellar prosthesis according to claim 1, wherein said body includes a cylindrical portion extending from said circular edge and joining said body surface.

3. A patellar prosthesis according to claim 1, wherein said post means comprises a central post terminating in a free end, said post having a plurality of longitudinal grooves extending to said free end.

4. A patellar prosthesis according to claim 3, wherein said central post has a passageway along said central axis extending to said free end.

5. A patellar prosthesis according to claim 3, wherein said central post has a plurality of annular grooves.

6. A patellar prosthesis according to claim 3, wherein said body surface has a plurality of concavities each having retention means including a wall extending from said body surface in a direction tapering toward said central axis.

7. The patellar prosthesis of claim 1, wherein said retention means includes a wall defining a portion of said concavity, said wall extending from said body surface in a direction tapering toward said central axis.

8. The patellar prosthesis of claim 7, wherein said concavity is provided with a roughened surface.

9. A one-piece patellar prosthesis adapted to be implanted in a prepared patella with bone cement comprising:
   (a) a dome having an outwardly facing surface, convexly curved throughout, positioned for sliding engagement with a femoral prosthesis, said dome terminating at its radial outer extent in a circular edge defining a plane, said dome having a central axis perpendicular to said plane;
   (b) a body having a surface facing away from said outwardly facing surface, said body extending to said circular edge and said body surface having a first central area in proximity to said central axis spaced from said plane by a predetermined amount and other areas extending radially outwardly from said central axis, said other areas having at least one concavity with a reverse taper surface for positive engagement with said bone cement, said body surface tapering toward said plane; and
   (c) a central post extending from said body surface along said central axis.

10. The patellar prosthesis of claim 9, wherein said central post has a plurality of grooves parallel to said central axis.

11. A patellar prosthesis according to claim 10, wherein said central post has a plurality of annular grooves.

12. A patellar prosthesis according to claim 9, wherein said body surface has a plurality of concavities each having retention means for engagement with said bone cement including a wall extending from said body surface in a direction tapering toward said central axis.

13. A patellar prosthesis according to claim 12, wherein said retention means is provided with a surface which is roughened.

14. A patellar prosthesis comprising:
  (a) a central post extending along a longitudinal axis and
  (b) a body portion extending from said central post, said body portion having,
    (i) a first side extending outwardly from said longitudinal axis and tapering away from said central post to an outer peripheral edge, said first side having a plurality of concavities having reverse taper surfaces; and
    (ii) a second side having a domed surface, convexly curved throughout, with an apex lying on said longitudinal axis, said apex being spaced axially from said central post further than any other portion of said domed surface.

15. The patellar prosthesis of claim 14, wherein said central post has a plurality of longitudinal grooves.

16. The patellar prosthesis of claim 15, wherein said central post has a passageway lying on said longitudinal axis.

17. A patellar prosthesis according to claim 15, wherein said central post has a plurality of annular grooves.

18. The patellar prosthesis of claim 15, wherein said longitudinal grooves are aligned with said concavities.

19. A patellar prosthesis of claim 14, wherein said retention means includes a wall defining a portion of each of said concavities, said wall extending from said first side toward said second side and tapering toward said longitudinal axis.

20. A patellar prosthesis of claim 19, wherein said retention means are provided with surfaces which are roughened.

* * * * *